March 18, 1958 R. HUMMEL Plant Pat. 1,691
STRAWBERRY PLANT
Filed Aug. 24, 1956 2 Sheets-Sheet 1
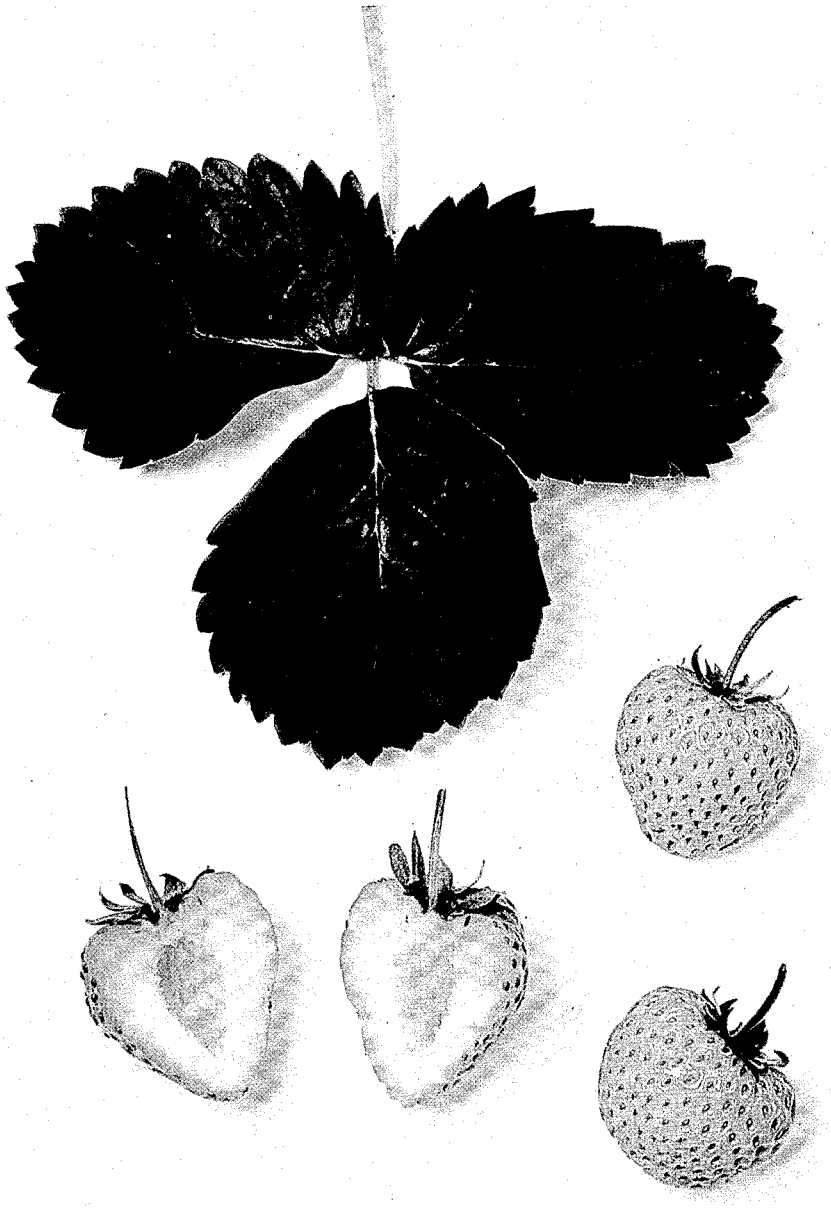
INVENTOR
Reinhold Hummel
BY Robert Cobb
ATTORNEYS March 18, 1958 R. HUMMEL Plant Pat. 1,691
STRAWBERRY PLANT
Filed Aug. 24, 1956 2 Sheets-Sheet 2
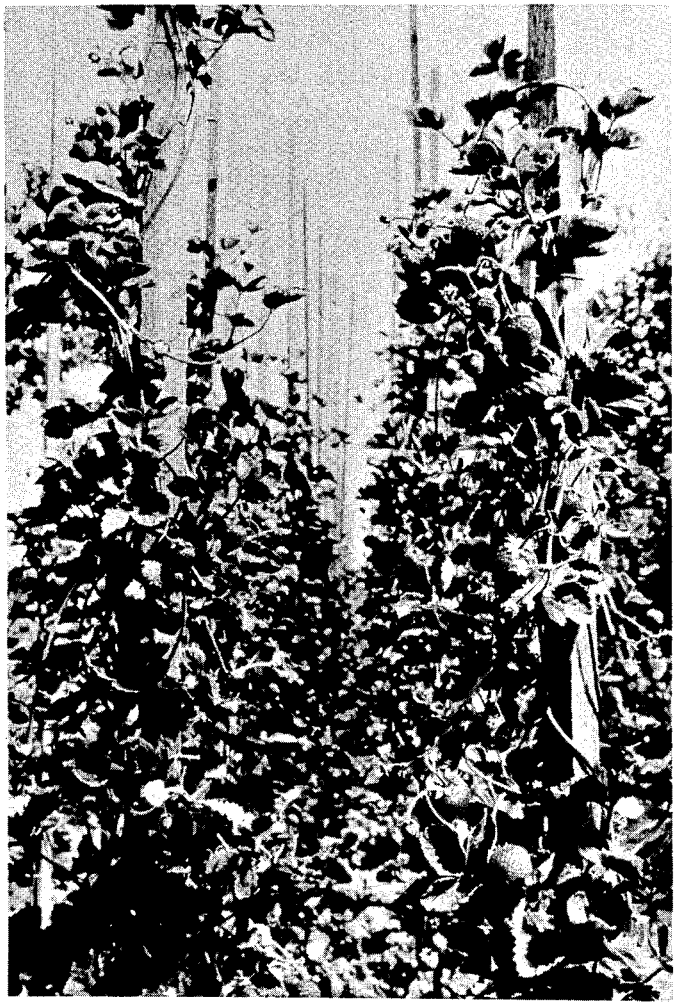
INVENTOR
Reinhold Hummel
BY Robert Cobb
ATTORNEYS United States Patent Office Plant Pat. 1,691
Patented Mar. 18, 1958

1,691

STRAWBERRY PLANT

Reinhold Hummel, Stuttgart-Weilindorf, Germany

Application August 24, 1956, Serial No. 606,179

Claims priority, application Germany November 29, 1955

1 Claim. (Cl. 47—62)

The present invention relates to a new and distinct variety of strawberry plant of the ever-bearing class, but having the peculiar property of being capable to be trained on poles or the like and thus to have a plant vegetation comparable to a climber, the term "climber," as used herein, being applicable in a non-technical sense as commonly applied to some plants such as climbing roses and the like which are not stirctly self-supporting. Said variety was originated by me by cross-breeding selected unnamed and unpatented seedlings derived from crossing the variety named "Holstein" (unpatented) with the variety named "Sonja Horstmann" (unpatented).

The primary objective of this breeding was to produce a new strawberry variety which would extend its growth and grow on poles, trellises, ladders and the like, as distinguished from those varieties heretofore known which are strictly ground-running.

Ancillary to the primary objective aforesaid was the further important problem of producing a new strawberry variety in which its extending and tall-running habit would not adversely affect its fruit-bearing qualities. These objectives have been fully achieved, along with other important improved characteristics which all together represent a unique and remarkable combination which definitely distinguishes my new variety from its antecedents, as well as from all other varieties of which I am aware.

As a result of the tall-running or so-called climbing habit and of the pole-training of my new variety, which in itself is unique in the field of strawberry plants, it is entirely possible and practical to grow my new variety in small gardens, as well as on balcony trellises and anywhere where little or no garden space is available, even in a mere earthen pot.

Of equal importance is the fact that my new variety is ever-bearing and accordingly blooms, bears, extends its growth in the form of runners, and reblooms, bears and continues to extend its growth, etc. in regular periods from Spring until first frosts, which, in Germany, covers a prolonged period running from May until late Fall.

As the foundation for the breeding of my new strawberry variety, I initially crossed the ever-bearing variety "Holstein" (unpatented) with the variety "Sonja Horstmann" (unpatented) which usually bears twice per season. The "Holstein" variety was chosen because of its long-reaching runners, although that variety normally produces fruit of medium size only once per season. On the other hand, "Sonja Horstmann" was used as the other basic parent because of its characteristic production of fruit of large size and the good and distinctive aroma of its fruit. The latter variety normally has no runners and is customarily reproduced by division, but if the plants are left alone, they will put out strong runners.

My experimentation and research with the basic parent varieties extended over a period of some seven years, and from seedlings derived from crossing these varieties, I selected the best strains which were then crossed again. The second crossings produced some 15,000 seedlings from which I selected a single plant that was outstanding and that showed the desired characteristics which I was endeavoring to achieve as aforementioned. This single mother-plant showed no peculiar leaf-growth, but bore long, strong runners which developed very early while supported on a ladder, and which quickly bloomed, bore fruit, and thereafter themselves put out further runners. These latter runners also exhibited a running habit corresponding to the first runners, without stunting or otherwise adversely affecting the first runners, and, under the same conditions, the cycle of blooming and fruit production repeated itself on the succeeding runners.

Continued tests and observations conclusively demonstrated that my new variety would attain a height of 6 feet or more when mature, and the plant repeats its blooming, bearing of fruit, and extension of growth in the form of new runners in regular periods of succession from Spring until first frosts.

The fruit of my new variety consistently attains a medium size, is blunt-cone-shaped, has a glistening deep red color, a very good aroma, and is endowed with superior keeping qualities. The plant itself is strong-rooted and unusually winter-hardy.

Asexual reproduction of my new variety by rooting of the layers or stolons, as performed by me at Stuttgart-Weilindorf, Germany, shows that the foregoing characteristics and distinctions come true to form and are established and transmitted through succeeding propagations.

The essential distinctions between my new variety and other ordinary strawberry varieties are that my new variety is capable of being trained on espalier and that the runners from the mother-plant bloom and bear fruit immediately after the production of the first leaves of the young plants, without waiting for the following year as is the case with ordinary strawberry varieties. The mother-plant of my new variety subsequently nourishes a succeeding chain of runners, it blooms strongly and bears fruit, even when its growth of leaves is not substantial.

It is thus possible now, by means of my new variety, to obtain on a reduced soil space, through a suitable trellising, a production of strawberries from Spring until first frosts.

The accompanying drawings show typical specimen plants of my new strawberry variety, depicting in black-and-white their tall-running habit, as well as the foliage, flowers and fruit in different stages of development, and also illustrating in color typical speciments of the fruit and foliage, with one of the fruit specimens shown in cross-section.

The following is a detailed botanical and technical description of my new variety, with color terminology in accordance with the Horticultural Colour Guide (hereinafter abbreviated as "H. C. G."), as indicated, except where general color terms of ordinary dictionary significance are obvious:

Location where grown and observed: Stuttgart-Weilindorf, Germany.

Dates of first and last picking: May 25th–October 15th.

*Plant*

Growth: Mother-plant—medium vigor. Runners—outstanding vigor. Roots—vigorous. Outstanding winter-hardiness.

Leaves: Fairly numerous; erect; wide.

*Leaflets.*—Wrinkled; cup-shaped. Petiole of terminal leaflet 4 times longer than that of the lateral leaflets.

*Serrations.*—Wide. About twenty fairly regular ogival serrations on every leaflet.

*Biometric constants:*

$$\text{Ratio } \frac{\text{Length of terminal leaflet}}{\text{Length of lateral leaflet}} = 1.1$$

$$\text{Ratio } \frac{\text{Length of terminal leaflet}}{\text{Width of terminal leaflet}} = 1.02$$

*Petiole.*—Average length, 12 cm. Average diameter, 3 mm. No bracts; rigid; deep groove.

*Color.*—Lettuce Green, Plate 861, page 176, vol. 2 (H. C. G.).

*Pubescence.*—Medium on petioles and leaf veins; wanting on leaf surface.

*Leaflet surface.*—Upper: glossy; wrinkled; color—Parsley Green, Plate 0962, page 193, vol. 2 (H. C. G.). Lower: color—Parsley Green, page 193, Plate 0962/2 (vol. 2, H. C. G.).

Runners: Appear before first blooms; extremely vigorous; more than 2 yards at end of season. Frequent secondary runners from rosettes or scales. Diameter, 5 mm.; average distance between rosettes, 29 cm. Flower stems on rosettes after opening of their first leaves. When the runners are trellised, growth of adventitious roots is inhibited but growth of rosettes is normal.

Inflorescence:

(*a*) *Mother-plant.*—Flower stem disengaged from the leaves, erect, with abundant and clear-colored pubescence; numerous corymbs. Average height from base to top of flower-stem, 19 cm. Average distance between base of flower-stem and insertion point of first corymb, 10 cm. Thickness of flower-stem, 3 mm. Bracts—lanceolated. 2–4 cymes per flower-stem. Average number of flowers per flower-stem, 8.5.

(*b*) *Rosettes.*—Flower stem generally with single corymb. Other characteristics similar to that of mother-plant.

Bloom: Ever-bearing variety.

*Date first bloom of mother-plant.*—April 20th–25th.

*Date first bloom of runners' rosettes.*—About June 5th.

Flowers:

*Diameter.*—Primary flowers, 2.5 cm. Secondary flowers, 1.7 cm.

*Petals.*—Rounded; bulging shape; little differentiated edges. Number per flower—medium.

*Filaments of stamens.*—Fairly long.

*Pollen.*—Abundant.

Fruit:

*Condition when described.*—Prime (end of May).

*Size.*—Medium. Average length, 2.9 cm. Average width, 2.6 cm. Average thickness, 1.7 cm.

*Form.*—Blunt-conical; regular.

*Stems.*—Fairly long; erect at first, then stooping. Pubescence—abundant.

*Calyx.*—Even with surface; tenacious. Average diameter, 2.3. Segments, 5–6; length, 7 mm.; width, 4 mm.; form—lanceolate.

*Epicalyx.*—Segments, 5–7; 6 mm. long; 2.5 mm. wide; form—narrowly oval.

*Color of induviae (calyx epicalyx).*—Upper surface—Sheeles Green, Plate 860/1, page 175, vol. 2 (H. C. G.). Lower surface—Pod Green, Plate 061, page 120, vol. 2 (H. C. G.). Periphery—Lettuce Green, Plate 861/2, page 176, vol. 2 (H. C. G.).

*Fruit surface.*—Very glossy. Color—Cardinal Red, Plate 822, page 168, vol. 2 (H. C. G.).

*Seeds.*—Inserted in hollows. Color—Cardinal Red, Plate 822, page 168, vol. 2 (H. C. G.).

*Flesh.*—Core: color—Scarlet Red, Plate 19/2, page 19, vol. 2 (H. C. G.). Surface: color—Signal Red, Plate 719, page 93, vol. 2 (H. C. G.). Texture—firm; fine; homogenous; juicy.

*Flavor.*—Very rich and sugary.

*Quality*—Excellent.

*Use.*—Market; dessert.

I claim:

A new and distinct variety of strawberry plant, substantially as herein shown and described, characterized particularly as to novelty by its ever-blooming and ever-bearing habits, its habit of initially reducing its leaf growth while producing and nourishing rapid-growing runners in succeeding chains of extended growth, said runners having the habit of reblooming and refruiting from Spring until frosts and being capable of being trained on and supported by poles and the like, its good winter-hardiness, and the blunt-cone shape, glistening deep-red color, good aroma and superior keeping qualities of its fruit.

No references cited.